US007607596B1

(12) United States Patent
Ghebre-Sellassie et al.

(10) Patent No.: US 7,607,596 B1
(45) Date of Patent: Oct. 27, 2009

(54) PROCESS FOR ENHANCING THE SOLUBILITY OF POORLY SOLUBLE DRUGS

(75) Inventors: Isaac Ghebre-Sellassie, Morris Plains, NJ (US); Hibrenigus Terefe, Somerville, NJ (US)

(73) Assignee: Exxpharma, LLC, Somerville, NJ (US)

( * ) Notice: Subject to any disclaimer, the term of this patent is extended or adjusted under 35 U.S.C. 154(b) by 20 days.

(21) Appl. No.: 12/072,224

(22) Filed: Feb. 25, 2008

Related U.S. Application Data

(60) Provisional application No. 60/905,781, filed on Mar. 7, 2007.

(51) Int. Cl.
*B02C 1/00* (2006.01)
*B02C 21/00* (2006.01)

(52) U.S. Cl. .............................. 241/21; 241/23; 241/29

(58) Field of Classification Search .................. 241/21, 241/23, 29
See application file for complete search history.

(56) References Cited

U.S. PATENT DOCUMENTS

| | | | |
|---|---|---|---|
| 4,801,460 | A | 1/1989 | Goertz et al. |
| 5,240,400 | A | 8/1993 | Fujimoto et al. |
| 5,456,923 | A | 10/1995 | Nakamichi et al. |
| 6,238,710 | B1 | 5/2001 | Song et al. |
| 6,499,984 | B1 | 12/2002 | Ghebre-Sellassie et al. |
| 2003/0090039 | A1 | 5/2003 | Ghebre-Sellassie et al. |
| 2005/0008704 | A1 | 1/2005 | Ray et al. |
| 2005/0238721 | A1 | 10/2005 | Acquarulo et al. |
| 2006/0006258 | A1 | 1/2006 | Remon et al. |
| 2006/0057073 | A1 | 3/2006 | Lintz et al. |

*Primary Examiner*—Faye Francis
(74) *Attorney, Agent, or Firm*—Jack Matalon

(57) ABSTRACT

The solubility/dissolution rate of a poorly soluble drug is enhanced by a process that utilizes a twin-screw extruder containing (i) a feed zone containing a first liquid and powder feed stations; (ii) a grinding/mixing zone containing a second liquid feed port located at an upstream portion of such zone; (iii) a granulation zone containing a second powder feed station located at an upstream portion of such zone and a third liquid feed port located at a downstream portion of such zone; and (iv) a wet milling zone.

18 Claims, No Drawings

PROCESS FOR ENHANCING THE SOLUBILITY OF POORLY SOLUBLE DRUGS

CROSS-REFERENCE TO RELATED APPLICATION

This application claims the benefit of Provisional Application Ser. No. 60/905,781, filed Mar. 7, 2007.

FIELD OF THE INVENTION

The invention pertains to a novel process and composition that produces solutions and nano-suspensions to enhance the dissolution rate/solubility of poorly soluble drugs as well as to the solubilized drugs produced by carrying out such process, and are subsequently processed into oral dosage forms, such as suspensions, emulsions, sachets, pellets, tablets or capsules.

BACKGROUND OF THE INVENTION

It is estimated that about 40% of drug candidates fail to advance through the clinical drug development process due to poor solubility, poor permeability or both. In an attempt to overcome the solubility issue, pharmaceutical scientists have been exploring numerous technologies, some of which have led to considerable success. Some of the manufacturing processes that were commonly used to increase the dissolution rates and enhance the solubility of poorly soluble drugs include particle size reduction, crystal modification, co-crystals, polymeric entrapment and filling of liquid and semi-solid drug formulations in soft and hard gelatin capsules. All of these commonly employed processes, however, have serious limitations. Some of these processes are labor intensive, pose serious challenge during scale up and/or utilize very expensive equipment/process, which renders them of limited use when cost of production is considered. The rest are in general associated with significant drug product stability or environmental issues. It is apparent, therefore, that a cost-effective manufacturing process and composition that overcome the limitations of the prior art is lacking, and is the subject of the present invention.

BENEFITS OF THE INVENTION

The present invention, which utilizes a twin screw grinder/mixer (TSGM) and solubility enhancers, does not only overcome the physical/chemical stability issues associated with the drug formulations of the prior art, but it also permits the continuous manufacture of poorly soluble drug products that have enhanced dissolution rates/solubilities in a cost-effective manner through the elimination of a number of separate unit operations that are time-consuming and labor-intensive. The process also brings about an intimate contact between the drug particles/molecules and the solubilizing agents in a highly efficient manner under controlled pressure and temperature, thereby resulting in the production of uniform suspensions or well defined granules that contain "discrete particles or molecules" surrounded by dissolution rate/solubility enhancers. Indeed, the invention provides a very uniform distribution of the formulation components throughout the liquid/semi-solid solution/suspension, or solid granulated material that is rarely met by any prior art.

OBJECT OF THE INVENTION

The object of the invention is to describe a manufacturing process and composition that utilize a TSGM and specific formulation components to enhance the dissolution rate/solubility of poorly soluble drugs. Any poorly soluble drug will benefit from the invention. The drug may fall into one or more of the following classes of drugs: abortifacient/interceptive agents; ace-inhibitors; α-and β-adrenergenic agonists; α- and β-adrenergic blockers; adrenocortical steroids and suppressants; adrenocorticotropic hormones; alcohol deterrents; aldose reductase inhibitors; aldosterone antagonists; ampa receptor antagonists; anabolics; analgesics (narcotic and non-narcotic); angiotension II receptors; anorexics; antacids; anthelmintics; antiacne agents; antiallergics; antialopecia agents; antiamebics; antiandrogens; antianginals; antiarrhythmics; antiarthritics; antirheumatics; antibiotics (natural and synthetic); anticoagulants; anticonvulsants; antidepressnts; antidiabetics; antidiarrheal; antidiuretics; antiemetics; antiglaucoma agents; antigout agents; antihistaminics; antihyperlipoproteinemics; antihyperparathyroids; antiperphosphatemics; antihypertensives; antiperthyroids; antihypotensives; antihypothyroid agents; antiinflammatories (non-steroidal and steroidal); antimalarials; antimigraine agents; anti-muscarinics; antineoplastics; antiobesity agents; antiobsessional agents; antiosteoporotic agents; antiparkinosonian agents; antiprotozoal agents; antipruritics; antisporiatics; antipsychotics; antipyretics; antispasmodics; antithrombotics; antitussives; antiulceratives; antivirals; anxiolytics; calcium channel blockers; calcium regulators; carbonic anhydrase inhibitors; cardioprotectives; cardiotonics; choleretic agents; cholinergics; cholinesterase inhibitors; central nervous system stimulants; contraceptives; decongestants; diuretics; dopamine receptor agonists and antagonists; expectorants; fibrinogen receptor antagonist; glucocorticoids; hematinics; immunomodulators; immunosuppressants; monoamine oxidase inhibitors; mucolytics; muscle relaxants; mydriatics; narcotic antagonists; neuromuscular blocking agents; neuroprotectives; nootropics; prolactin inhibitors; reverse transcriptase inhibitors; sedatives/hypnotics; serotonin receptor agonists and antagonists; serotonin uptake inhibitors; steroids, thrombolytics; vasodilators; and vitamins.

Exemplary poorly soluble drugs that will benefit from the invention include: raloxifene, paroxetine, glimepiride, anagrelide, modafanil, paroxetine, cabergoline, replaginide, glipizide, benzodiazapines, clofibrate, chlorpheniramine, digoxine, diphenhydramine, egrotamine, estradiol, fenofibrate, griseofulvin, hydrochlothizide, hydrocortisone, isosorbide, medrogeston, oxyphenbutazone, prednisilone, prednisone, polythiazide, progensterone, spirono-lactone, tolbutamide, 10,11-dihydro-5H-dibenzo-(a,d)cycloheptene-5-carboxamide, and 5H-dibenzo-(a,d)cycloheptene-5-carboxamide.

SUMMARY OF THE INVENTION

The present invention relates to a continuous process and composition (and the product produced by such process) that enhance the dissolution rates/solubilities of poorly soluble drugs. A TWGM converts a mixture of liquids and powders into solutions/suspensions to be used as they are, or optionally further processed in line, or through a granulator arranged in series with the TWGM into granulations by mixing the solutions/suspensions with powder components.

DETAILS OF THE PRESENT INVENTION

The present invention pertains to a novel process and the product produced by such process. The process is a continuous grinding/mixing process that is used to enhance the dissolution rate/solubility of a poorly soluble drug, comprising the steps of:

(a) providing a counter-rotating TSGM containing temperature control means and the following zones in sequential communication with one another: (i) a liquid/powder feed zone containing a first liquid/powder feed station; (ii) a grinding/mixing zone containing a second liquid feed port located at an upstream portion of such zone; or (i) a liquid/powder feed zone containing a first liquid/powder feed station; (ii) a grinding/mixing zone containing a second liquid feed port located at an upstream portion of such zone; (iii) a granulation zone containing a second powder feed station located at an upstream portion of such zone and a third liquid feed port located at a downstream portion of such zone; and (iv) a wet milling zone; or (i) a liquid/powder feed zone containing a first liquid/powder feed station; (ii) a grinding/mixing zone containing a second liquid feed port located at an upstream portion of such zone; (iii) a mixer/granulator arranged in series with the TSGM; and (iv) a wet milling step.

(b) feeding into the first powder feed station a powder comprising the drug and 0 to about 1000 parts, per 100 parts of the drug, of one or more first excipients selected from the group consisting of solubilizing agents, complexing agents, buffering agents, polymers, plasticizers, co-solvents, surfactants, self-emulsifiers, hydrophilic waxes, fatty acids, fatty alcohols and mixtures thereof;

(c) injecting into the first and/or second liquid ports 0 to about 1000 parts, per 100 parts of the powder fed into the first powder station in step (b), of a pharmaceutically acceptable liquid containing 0 to about 1000 parts, per 100 parts of the drug of one or more excipients selected from the group consisting of solubilizing agents, complexing agents, buffering agents, polymers, plasticizers, surfactants, self-emulsifiers, co-solvents, hydrophilic waxes, fatty acids, fatty alcohols and mixtures thereof;

(d) grinding/mixing in the grinding/mixing zone the drug and any first excipients employed in step (b) and any liquid employed in step (c) at a temperature of about 20° to less than 100° C.;

(e) conveying the material resulting from step (d) either into a separate container for storage/dispenser and packaging, OR into the granulation zone within the TSGM or in a continuous granulator arranged in series with the TSGM;

(f) feeding into the second powder station of the TSGM or the first powder station of another mixer/granulator one or more second excipients selected from the group consisting of fillers, glidants, binders, lubricants, adsorbents, enteric coating agents, anti-caking agents, anti-oxidants, anti-adherents, disintegrants, flavorants, stabilizers, colorants, preservatives, carrier materials, and mixtures thereof;

(g) injecting into the second liquid port a binder/colorant solution in the amount of 0 to about 1000 parts per 100 parts of the material conveyed into the granulation zone of the TSGM, or the mixer/granulator arranged in series;

(h) granulating the material and any binder solution added in the granulation step;

(i) conveying the granulated material resulting from step (h) into the wet milling zone of the TSGM or the mixer granulator in series and wet milling the granulated material in such zone;

(j) discharging the granulated material resulting from step (h); and (k) drying the discharged granulated material.

The TSGM will contain temperature control means (usually in the form of a jacket through which a heat exchange fluid will flow) to maintain the zones, especially the grinding/mixing zone, at a temperature of about 20 to less than about 100° C. (optionally, the TSGM may contain a vent to remove moisture and volatiles). The TSGM screws will be of the type that intermesh and will be counter-rotating. Optionally, the screws could be co-rotating. However, counter-rotating intermeshing screws are preferred, due to, among other characteristics, the local areas of high shear in the intermeshing region, which results in effective dispersive mixing, and the milling type of intermeshing, as in a two roll mill, which draws the material through the calendar gap and exposes the material to high stresses. Although the dimensions of the TSGM are not critical, it should be large enough to handle a reasonable volume of API, liquids and excipients on a continuous basis. As a guide, the screws will generally be about 12 mm to about 135 mm. The overall length of the TSGM is typically designed to be a multiple of the screw diameter. Generally, the overall length of the TSGM to the screw diameter is between about 20:1 and about 60:1. The length of the individual zones within the TSGM is generally in multiples of 3 to 4D. The pitch of the element that conveys the material from one zone to the next is generally between about 15 mm and about 180 mm depending on the requirements for the grinding/mixing step and the grinding/mixing/granulation processes.

Several different screw designs can be utilized. The screw sizes, threads, pitches, and angles of contact with the housing of the TSGM may vary depending on the particular poorly soluble drug and excipients.

In general, the manufacturing processes operate at room temperature. However, the temperature may be raised, e.g., to a temperature of about 30 to less than about 100° C., to increase the solubility of the poorly soluble drug in the additives, or for any other reason to affect product properties. Temperature regulation within the TSGM may be maintained by a heat exchange fluid circulated in a jacket surrounding the housing of the TSGM. Alternatively, electrical heating and fluid cooling may be used.

In the feed zone of the TSGM, there will be a first liquid and first powder feed station in communication with the beginning of the feed zone. The first powder feed station may be disposed behind or on top of the powder feed zone, but is preferably disposed behind the powder feed zone. Powder may be fed into the powder feed station and thence into the powder feed zone from the top by gravity feed, or horizontally with the help of a side-screw)feeder from behind. External to the first powder feed station will be disposed the usual means for metering amounts of powder to the station.

The grinding/mixing zone will contain a second liquid port disposed above or below an upstream portion of the grinding/mixing zone. The usual means for metering amounts of liquid into the second liquid port will be disposed outside the TSGM.

The granulation zone is in sequential communication with, and disposed downstream of the granulation/mixing zone of the TSGM or another continuous granulator located in series with the TSGM. The granulation zone will contain a second powder feed station in communication with, and disposed in an upstream portion of, such zone and a third liquid port in communication with, and disposed in a downstream portion of, such zone. The usual means for metering amounts of liquid into the third liquid port will be disposed outside the TSGM. External to the second powder station will be disposed the usual means for metering amounts of powder to the station.

Typically, a die or end plate is kept at the end of the TSGM during the grinding/mixing phase only, if the end product desired is a solution/suspension, or if the solution/suspension so produced is directed in line to the second continuous graulator for granulation purposes. However, if granulation is carried out directly within the TSGM, the end plate is removed during grinding/mixing/granulation phases so that the granulated product may be wet-milled and discharged at a relatively low pressure. The TSGM screw shafts are made to protrude at the end to assist the wet-milling process. Optionally, the protruded shafts may be anchored on a detached end plate firmly held in line with the barrels to keep the shafts in place and prevent wobbling during material processing.

Steps (b), (c) and (d) of the process of the invention actually encompasses two distinct processes:

Process I: In this process, the powdered poorly soluble drug together with the desired first excipients are pre-blended with conventional pharmaceutical blending equipment (e.g., V-blender) and the pre-blend is admitted through the first powder feed station into the feed zone and thence into the grinding/mixing zone. Alternatively, individual powders could be separately introduced into the feed zone concurrently at predetermined rates from more than one powder feeder and blended in the TSGM as they are conveyed towards the grinding/mixing zone. The particular first excipients and the amounts thereof are a matter of choice; those skilled in the art will select the first excipients and utilize them in such amounts as they deem appropriate for the poorly soluble drug whose solubility is to be enhanced.

Typically, the powder(s) will comprise the drug and up to about 1000 parts, preferably about 100 to about 800 parts, of the first excipients per 100 parts of the drug. Concurrent with, or slightly after, the powder(s) is/are fed through the first powder feed station into the feed zone and thence into the grinding/mixing zone, the liquid recited in step (c) is injected into the first or second liquid port.

For the purposes of Process I, the liquid injected into the first and liquid liquids port will be a pure pharmaceutically acceptable liquid, preferably water, and will not contain any excipients. The liquid injected into the first and second liquid ports will typically be utilized in an amount of up to about 1000 parts, preferably about 100 to about 800 parts, per 100 parts of the pre-blended powder fed into the grinding/mixing zone to produce liquid solutions/suspensions.

Process II: In this process, the powdered poorly soluble drug alone (i.e., not pre-blended with any excipients) is admitted through the first powder feed station into the feed zone and thence into the grinding/mixing zone. Concurrent with, or slightly before or after, the powdered drug is fed through the first powder feed station into the feed zone and thence into the grinding/mixing zone, the liquid recited in step (c) is injected into the first and/or second liquid port.

For the purposes of Process II, the liquid injected into the first and second liquid ports will be a pharmaceutically acceptable liquid, preferably water, and will contain one or more second excipients. The particular second excipients and the amounts thereof are a matter of choice; those skilled in the art will select the second excipients and utilize them in such amounts as they deem appropriate for the poorly soluble drug whose dissolution rate/solubility is to be enhanced. Typically, the liquid will contain up to about 1000 parts, preferably about 100 to about 800 parts, of the second excipients per 100 parts of the drug and will be utilized in an amount of up to about 1000 parts, preferably about 100 to about 800 parts, per 100 parts of the drug admitted into the grinding/mixing zone. In both Process I and Process II, the temperatures of the liquid and grinding/mixing zone could be set between room temperature and 100° C.

An alternative to Process I is to admit the powdered drug and first excipients, either as a preblend or as separate components into the powder feed zone and thence into the grinding/mixing zone, omit the injection of any liquid into the first and second liquid ports, and carry out the grinding/mixing of the powdered drug and first excipients at an elevated temperature of less than about 100° C., e.g., about 30 to about 80° C. Optionally, liquids may also be injected at the first and/or second liquid ports, if desired.

In order to effectively grind/mix the powders in the absence of any liquid, it is preferred that the first excipients include one or more high boiling liquids, low melting additives, and/or thermoplastic polymers. Typically, the excipients will be employed in an amount of 0.1 to 999 parts, preferably 0.5 to 500 parts and most preferably, 1 to 50 parts per part of the poorly soluble drug. Suitable thermoplastic polymers include polyethylenes, polypropylenes, celluloses, ethylene-propylene copolymers, polyacrylates, polymethacrylates, ethyl vinyl acetate, ethylene vinyl alcohol, polystyrene, polyvinylchloride, acrylonitrile-butadiene-styrene, polyvinyl-pyrrolidone and mixtures of the foregoing polymers.

It may also be desirable that the first excipients include one or more plasticizers to lower the glass transition temperature of the thermoplastic polymer, and/or solubilize the poorly soluble drug. Suitable plasticizers are those that are generally used as plasticizers for film coating compositions in the pharmaceutical field. Exemplary plasticizers include cetanol, medium chain triglycerides, polyoxyethylene-polyoxy-propylene glycol (Pluronic), macrogols (200, 300, 400, 600, 1000, 1500, 1540, 4000, 6000, 20000), triacetin, triethyl citrate, diethyl phthalate, hydrogenated castor oil, etc. The amount of the plasticizer that is used will be dependent upon the particular poorly soluble drug and the particular polymer(s) that are used, but is approximately 1 to 80 wt. %, preferably 5 to 50 wt. %, based on the weight of the polymer(s).

Suitable first and second excipients include sorbitan fatty acid esters, phosphatides, lecithin, gum acacia, gum tragacanth, polyoxyethylenesorbitan monooleate, ethoxylated fatty acid esters of sorbitan, polyoxyethylated fats, polyoxyethylated oleotriglycerides, linolizated oleotriglyclycericides, polyethylene oxide condensation products of fatty alcohols, alkylphenols, hydroxypropylmethylcellulose phthalate, hydroxypropyl-methylcellulose acetate succinate, carboxymethylcellulose phthalate, cellulose acetate phthalate, Eudragit acrylic copolymers, methacrylic copolymer LD, methacrylic copolymer S, methacrylic copolymer RS, polyvinyl alcohol, high molecular weight polyethylene glycols, aminoalkyl methacrylate copolymer, poly(vinyl acetal) diethylaminoacetate, ethyl vinyl acetate, ethylene vinyl alcohol, acrylonitrile-butadiene-styrene, polystyrene, polyvinylpyrrolidone, ethylcellulose, methylcellulose, hydroxypropylcellulose, hydroxy-propylmethylcellulose, carboxymethylcellulose sodium, dextrin, pullulan, sodium alginate, propylene glycol alginate, agar powder, gelatin, glucomannan, cetanol, polyoxyethylene-polyoxypropylene glycols, polyvinyl chloride, triacetin, triethyl citrate, polyoxyethylene acids, polyoxyethylene alcohols, phospholipids, block copolymers of polyethylene oxide and a poly[butyl (alkyl) acylate-co-alkyl) acrylic acid], mono-, di- and triglycerides, sodium carboxymethylcellulose, hydroxypropylmethylcellulose, hydroxyalkyl-α-, -β- and/or -γ-cyclodextrins, polyoxamers, polyoxysorbitan fatty acid esters, polyoxyethylene stearate, polyvinylpyrrolidone, polyoxyalkylene alkyl ethers, sodium croscarmellose, crospovidone, sodium starch glycolate and mixtures thereof.

Exemplary buffering agents that may be utilized for either the first or second excipients include amines, silicates, carbonates, oxides, phosphates, citrates, acetates, phthalates, bicarbonates, borates and mixtures thereof.

It should be understood that the choice of the first excipient need not be the same as the choice of the second excipient. In respect to the first excipient, the choice is made from those materials that are powders at room temperature for the purposes of practicing Process I. In respect to the second excipient, the choice is made from those materials that are liquids, or readily dissolve or disperse in the liquid that is to be injected in the first and second liquid ports for the purposes of practicing Process II.

Regardless of whether Process I or Process II is to be practiced, in step (f) of the process of the invention, one or more third excipients are fed into the second powder station and thence into the granulation zone wherein the third excipient is granulated with the mass that has been conveyed from the grinding/mixing zone. The third excipient may be the same or different material that is selected for the practice of Process I or Process II. Suitable third excipients include: fillers, glidants, lubricants, adsorbents, enteric coating agents, hydrophilic and hydrophobic excipients, drug release modifiers, pH modifiers, anti-caking agents, anti-oxidants, anti-adherents, disintegrants, flavorants, stabilizers, colorants, preservatives, carrier materials, and mixtures thereof.

Exemplary fillers include: cellulose derivatives, starches, dibasic calcium phosphate dihydrate, carnuba wax, calcium sulfate trihydrate, calcium sulfate dihydrate, calcium carbonate, lactose, dextrose, sucrose, mannitol, xylitol, sorbitol and mixtures thereof.

Exemplary lubricants include: magnesium stearate, calcium stearate, zinc stearate, talc, propylene glycol, polyethylene glycol, stearic acid vegetable oil, sodium benzoate, sodium lauryl sulfate, magnesium lauryl sulfate, mineral oil polyoxyethylene monostearate and mixtures thereof.

Exemplary co-solvents include propylene glycol, glycerin, polyethylene glycol, polyvinyl pyrrolidone and mixtures thereof.

Exemplary enteric coating agents include: hdroxypropylmethylcellulose phthalate, methacrylic acid-methacrylic acid copolymer, methyl methacrylate-methacrylic acid copolymer, polyvinyl acetate-phthalate, cellulose acetate phthalate and mixtures thereof.

Exemplary glidants include: silica, colloidal silica, magnesium trisilicate, powdered cellulose, starch, talc, tribasic calcium phosphate and mixtures thereof.

Exemplary disintegrants include natural starches, starch derivatives, cross-linked polyvinylpyrrolidone, alginic acid, sodium alginate, methacrylic acid-divinylbenzene copolymer salts, cross-linked carboxymethylcellulose, hydroxypropylcellulose, hydroxypropylmethylcellulose, croscarmellose sodium, sodium starch glycolate, polacrillin potassium, polyacrylates, magnesium aluminum silicate, bentonite and mixtures thereof.

Exemplary carrier materials include: cross-linked and non-cross-linked polyvinylpyrrolidone, carboxymethylamide, potassium methacrylate-divinylbenzene copolymer, polyvinyl alcohols, polyoxyethylene glycols, polyethylene glycols, sodium alginate, galactomannone, carboxypolymethylene, sodium carboxymethyl starch, sodium carboxymethyl cellulose, microcrystalline cellulose, polymerizates and co-polymerizates of acrylic acid and/or methacrylic acid and/or their esters, polyvinyl acetate, fats, oils, waxes, fatty alcohols, hydroxypropylmethylcellulose phthalate, hydroxypropylmethylcellulose acetate succinate, cellulose acetate phthalate, starch acetate phthalate, polyvinylacetate phthalate, carboxymethylcellulose, methylcellulose phthalate, methylcellulose succinate, ethylcellulose, ethylcellulose succinate, gluten, ethylcarboxyethylecellulose, ethylacrylate-maleic acid anhydride copolymer, maleic acid anhydride-vinylmethylether copolymer, styrene-maleic acid anhydride copolymer, 2-ethyl-hexylacrylate maleic acid anhydride, crotonic acid-vinyl acetate copolymer, glutamic acid/glutamic acid ester copolymer, carboxymethylethylcellulose glycerol monooctanoate, cellulose acetate succinate, polyarginine, polyethylenes, polypropylenes, polyethylene oxide, polyethylene terephthalate, poly(vinylisobutylether), polyvinylchloride, polyurethane and mixtures thereof.

During the granulation, it may be desirable to utilize a binder solution that may be injected into a third liquid port located in a downstream portion of the granulation zone. The binder solution is utilized in an amount of 0 to about 1000 parts, preferably (if used) in an amount of about 100 to about 800 parts, per 100 parts of the mass conveyed into the granulation zone from the grinding/mixing zone. If used, the binder solution will contain about 0.1 to about 50 wt. % of a suitable binder. Exemplary binders include: potato starch, wheat starch, corn starch, gum tragacanth, gum acacia, gelatin, methylcellulose, hydroxypropylcellulose, hydroxyethylcellulose, hydroxypropylmethylcellulose, pectin, polyvinylpyrrolidone, and mixtures thereof.

The granulated mass is conveyed into the wet-milling zone and is thereafter discharged as granules that are subsequently dried. Suitable methods of drying the granules include: fluidized-bed drying, rotary drying, tray drying, vacuum drying, radio-frequency drying and microwave drying.

The following nonlimiting examples shall serve to illustrate the various embodiments of the invention. Unless otherwise indicated to the contrary, all parts and percentages are on a weight basis.

EXAMPLE 1

Ketoprofen powder and distilled water were fed concurrently upstream in a counter-rotating 18 mm TSGM. The mixture was then subjected to intense grinding and homogenization at 200 rpm and 25° C. in the grinding/mixing zone of the TSGM to generate a viscous dispersion consisting of a solution/suspension. The dispersion was then used to granulate powdered microcrystalline cellulose that was fed downstream through a second feed port of the TSGM. The granulation was collected and dried overnight in an oven at 40° C. It was found that the dissolution rate of ketoprofen in 0.1 N HCl had increased two-fold, while its equilibrium solubility remained unchanged.

EXAMPLE 2

Ketoprofen powder and a 10% aqueous solution of Labrasol® were fed concurrently upstream in a counter-rotating 18 mm TSGM. The mixture was then subjected to intense grinding and homogenization at 200 rpm and 25° C. in the grinding/mixing zone of the TSGM to generate a viscous dispersion consisting of a solution/suspension. The dispersion was then used to granulate powdered micro-crystalline cellulose that was fed downstream through a second feed port of the TSGM. The granulation was collected and dried overnight in an oven at 40° C. It was found that the dissolution rate of ketoprofen in 0.1N HCl had increased two-fold, while its equilibrium solubility remained unchanged.

EXAMPLE 3

Ketoprofen powder and a 10% aqueous solution of Tween® 80 were fed concurrently upstream in a counter-rotating 18 mm TSGM. The mixture was then subjected to intense grinding and homogenization at 200 rpm and 25° C. in the grinding/mixing zone of the TSGM to generate a viscous dispersion consisting of a solution/suspension. The dispersion was then used to granulate powdered micro-crystalline cellulose that was fed downstream through a second feed port of the TSGM. The granulation was collected and dried overnight in an oven at 40° C. It was found that the dissolution rate of ketoprofen in 0.1N HCl had increased four-fold, while its equilibrium solubility increased two-fold.

EXAMPLE 4

Ketoprofen powder and a 10% aqueous solution of Capryol® 90 were fed concurrently upstream in a counter-rotating 18 mm TSGM. The mixture was then subjected to intense grinding and homogenization at 200 rpm and 25° C. in the grinding/mixing zone of the TSGM to generate a viscous dispersion consisting of a solution/suspension. The dispersion was then used to granulate powdered micro-crystalline cellulose that was fed downstream through a second feed port of the TSGM. The granulation was collected and dried overnight in an oven at 40° C. It was found that the dissolution rate of ketoprofen in 0.1N HCl had increased two-fold, while its equilibrium solubility remained unchanged.

EXAMPLE 5

Ketoprofen powder and a 10% aqueous solution of polyvinylpyrrolidone were fed concurrently upstream in a counter-rotating 18 mm TSGM. The mixture was then subjected to intense grinding and homogenization at 200 rpm and 25° C. in the grinding/mixing zone of the TSGM to generate a viscous dispersion consisting of a solution/suspension. The dispersion was then used to granulate powdered micro-crystalline cellulose that was fed downstream through a second feed port of the TSGM. The granulation was collected and dried overnight in an oven at 40° C. It was found that the dissolution rate of ketoprofen in 0.1N HCl had increased three-fold, while its equilibrium solubility increase two-fold.

What is claimed is:

1. A continuous process for enhancing the dissolution rate/solubility of a poorly soluble drug comprising the steps of:

(a) providing a twin-screw grinder/mixer containing temperature control means and the following zones in sequential communication with one another: (i) a feed zone containing a first liquid and powder feed stations; (ii) a grinding/mixing zone containing a second liquid feed port located at an upstream portion of such zone; or a second continuous granulator placed in series; (iii) a granulation zone containing a second powder feed station located at an upstream portion of such zone and a third liquid feed port located at a downstream portion of such zone; and (iv) a wet milling zone;

(b) feeding into the first powder feed station a powder comprising the drug and 0 to about 1000 parts, per 100 parts of the drug, of one or more first excipients selected from the group consisting of solubilizing agents, complexing agents, buffers, polymers, plasticizers, surfactants, self-emulsifiers, hydrophilic waxes, fatty acids, fatty alcohols and mixtures thereof;

(c) injecting into the first and second liquid ports 0 to about 1000 parts, per 100 parts of the powder fed into the first powder station in step (b), of a pharmaceutically acceptable liquid containing 0 to about 1000 parts, per 100 parts of the drug of one or more second excipients selected from the group consisting of solubilizing agents, complexing agents, buffers, polymers, plasticizers, surfactants, self-emulsifiers and mixtures thereof;

(d) grinding/mixing in the grinding/mixing zone the drug and any first excipients employed in step (b) and any liquid employed in step (c) at a temperature of about 20° to less than about 100° C.;

(e) conveying the material resulting from step (d) to the granulation zone;

(f) feeding into the second powder station one or more third excipients selected from the group consisting of fillers, glidants, lubricants, absorbents, enteric coating agents, anti-caking agents, anti-oxidants, anti-adherents, disintegrants, flavorants, stabilizers, colorants, preservatives, carrier materials, and mixtures thereof;

(g) injecting into the third liquid port a binder solution in the amount of 0 to about 1000 parts per 100 parts of the material conveyed into the granulation zone;

(h) granulating the material and any binder solution present in the granulation zone;

(i) conveying the granulated material resulting from step (h) into the wet milling zone and wet milling the granulated material in such zone;

(j) discharging the granulated material resulting from step (h); and (k) drying the discharged granulated material.

2. The process of claim 1 wherein the twin-screws of the twin-screw grinder/mixer intermesh and are co-rotating or counter-rotating.

3. The process of claim 1 wherein the first excipients are employed in step (b) in an amount of about 100 to about 800 parts per 100 parts of the drug and the liquid employed in step (c) comprises water containing 0 parts of the second excipients and is employed in an amount of about 100 to about 800 parts per 100 parts of the powder fed into the first powder station.

4. The process of claim 1 wherein the first excipients are employed in step (b) in an amount of 0 parts per 100 parts of the drug and the liquid is employed in step (c) in an amount of about 100 to about 800 parts per 100 parts of the drug, said liquid comprising a solution or a suspension containing about 100 to about 800 parts of the second excipients per 100 parts of the drug.

5. The process of claim 1 wherein the first excipients are employed in step (b) in an amount of about 100 to about 800 parts per 100 parts of the drug, the liquid is employed in step (c) in an amount of 0 parts and the granulating/mixing zone is maintained at a temperature of about 30 to about 80° C.

6. The process of claim 1 wherein the binder solution is employed in step (g) in an amount of about 100 to about 800 parts, per 100 parts of the material being granulated in the granulation zone.

7. The process of claim 6 wherein the binder comprises a polymer selected from the group consisting of potato starch, wheat starch, corn starch, gum tragacanth, gum acacia, gelatin, methylcellulose, hdroxypropylcellulose, hydroxyethylcellulose, hydroxypropylmethylcellulose, pectin, polyvinylpyrrolidone, and mixtures thereof.

8. The process of claim 1 wherein the poorly soluble drug is selected from the group consisting of the following classes of drugs: abortifacient/interceptive agents; ace-inhibitors; α-and β-adrenergenic agonists; α- and β-adrenergic blockers; adrenocortical steroids and suppressants; adrenocorticotropic hormones; alcohol deterrents; aldose reductase inhibitors; aldosterone antagonists; ampa receptor antagonists; anabolics; analgesics (narcotic and non-narcotic); angiotension II receptors; anorexics; antacids; anthelmintics; antiacne agents; antiallergics; antialopecia agents; antiamebics; antiandrogens; antianginals; antiarrhythmics; antiarthritics/antirheumatics; antibiotics (natural and synthetic); anticoagulants; anticonvulsants; antidepressnts; antidiabetics; antidiarrheal; antidiuretics; antiemetics; antiglaucoma agents; antigout agents; antihistaminics; antihyperlipoproteinemics; antihyperparathyroids; antiper-phosphatemics; antihypertensives; antiperthyroids; antihypotensives; antihypothyroid agents; antiinflammatories (non-steroidal and steroidal); antimalarials; antimigraine agents; anti-muscarinics; antineoplastics; antiobesity agents; antiobsessional agents; antiosteoporotic agents; antiparkinosonian agents; antiprotozoal agents; antipruritics; antisporiatics; antipsychotics; antipyretics; antispasmodics; antithrombotics; antitussives; antiulceratives; antivirals; anxiolytics; calcium channel blockers; calcium regulators; carbonic anhydrase inhibitors; cardioprotectives; cardiotonics; choleretic agents; cholinergics; cholinesterase inhibitors; central nervous system stimulants; contraceptives; decongestants; diuretics; dopamine receptor agonists and antagonists; expectorants; fibrinogen receptor antagonist; glucocorticoids; hematinics; immunomodulators; immunosuppressants; monoamine oxidase inhibitors; mucolytics; muscle relaxants; mydriatics; narcotic antagonists; neuromuscular blocking agents; neuroprotectives; nootropics; prolactin inhibitors; reverse transcriptase inhibitors; sedatives/hypnotics; serotonin receptor agonists and antagonists; serotonin uptake inhibitors; steroids, thrombolytics; vasodilators; and vitamins.

9. The process of claim 8 wherein the drug is selected from the group consisting of raloxifene, paroxetine, glimepiride, anagrelide, modafanil, paroxetine, cabergoline, replaginide, glipizide, benzodiazapines, clofibrate, chlorpheniramine, digoxine, diphen-hydramine, egrotamine, estradiol, fenofibrate, griseofulvin, hydrochlothizide, hydrocortisone, isosorbide, medrogeston, oxyphenbutazone, prednisilone, prednisone, polythiazide, progensterone, spirono-lactone, tolbutamide, 10,11-dihydro-5H-dibenzo-(a,d)cycloheptene-5-carboxamide, and 5H-dibenzo-(a,d)cycloheptene-5 carboxamide.

10. The process of claim 1 wherein the first and second excipients are independently are selected from the group consisting of sorbitan fatty acid esters, phospatides, lecithin, gum acacia, gum tragacanth, polyoxyethylenesorbitan monooleate, ethoxylated fatty acid esters of sorbitan, polyoxyethylated fats, polyoxyethylated oleotriglycerides, linolizated oleotriglyclycericides, polyethylene oxide condensation products of fatty alcohols, alkylphenols, hydroxypropylmethylcellulose phthalate, hydroxypropylmethylcellulose acetate succinate, carboxymethylcellulose phthalate, cellulose acetate phthalate, Eudragit acrylic copolymers, methacrylic copolymer LD, methacrylic copolymer S, methacrylic copolymer RS, polyvinyl alcohol, high molecular weight polyethylene glycols, aminoalkyl methacrylate copolymer, poly(vinyl acetal) diethylaminoacetate, ethyl vinyl acetate, ethylene vinyl alcohol, acrylonitrile-butadiene-styrene, polystyrene, polyvinylpyrrolidone, ethylcellulose, methylcellulose, hydroxylpropylcellulose, hydroxypropylmethylcellulose, carboxymethylcellulose sodium, dextrin, pullulan, sodium alginate, propylene glycol alginate, agar powder, gelatin, glucomannan, cetanol, polyoxyethylene-polyoxypropylene glycols, polyvinyl chloride, triacetin, triethyl citrate, polyoxyethylene acids, polyoxyethylene alcohols, phospholipids, block copolymers of polyethylene oxide and a poly[butyl (alkyl) acylate-co-(alkyl) acrylic acid], mono-,di- and tri-glycerides, sodium carboxymethylcellulose, hydroxypropylmethylcellulose, hydroxyalkyl-α-, -β- and/or -γ-cyclodextrins, polyoxamers, polyoxysorbitan fatty acid esters, polyoxyethylene stearate, polyvinylpyrrolidone, polyoxyalkylene alkyl ethers, sodium croscarmellose, crospovidone, sodium starch glycolate and mixtures thereof.

11. The process of claim 1 wherein the fillers are selected from the group consisting of microcrystalline cellulose, starch, modified starch, pregelatinized starch, dibasic calcium phosphate dihydrate, calcium sulfate trihydrate, calcium sulfate dihydrate, calcium carbonate, lactose, dextrose, sucrose, mannitol, xylitol, sorbitol and mixtures thereof.

12. The process of claim 1 wherein the lubricants are selected from the group consisting of magnesium stearate, calcium stearate, zinc stearate, talc, propylene glycol, polyethylene glycol, stearic acid vegetable oil, sodium benzoate, sodium lauryl sulfate, magnesium lauryl sulfate, mineral oil polyoxyethylene monostearate and mixtures thereof.

13. The process of claim 1 wherein the enteric coating agents are selected from the group consisting of hydroxypropylmethylcellulose phthalate, methacrylic acid-methacrylic acid copolymer, methyl methacrylate-methacrylic acid copolymer, polyvinyl acetate-phthalate, cellulose acetate phthalate and mixtures thereof.

14. The process of claim 1 wherein the glidants are selected from the group consisting of silica, colloidal silica, magnesium trisilicate, powdered cellulose, starch, talc, tribasic calcium phosphate and mixtures thereof.

15. The process of claim 1 wherein the disintegrants are selected from the group consisting of natural starches, starch derivatives, cross-linked polyvinylpyrrolidone, alginic acid, sodium alginate, methacrylic acid-divinylbenzene copolymer salts, cross-linked carboxymethylcellulose sodium, low substituted hydroxyl propyl cellulose, sodium starch glycolate, polacrillin potassium, magnesium aluminum silicate, bentonite and mixtures thereof.

16. The process of claim 1 wherein the carrier materials are selected from the group consisting of cross-linked and non-cross-linked polyvinylpyrrolidone, carboxymethylamide, potassium methacrylate-divinylbenzene copolymer, polyvinyl alcohols, polyoxyethylene glycols, polyethylene glycols, sodium alginate, galacto-mannone, carboxypolymethylene, sodium carboxymethyl starch, sodium carboxymethyl cellulose, microcrystalline cellulose, polymerizates and co-polymerizates of acrylic acid and/or methacrylic acid and/or their esters, polyvinyl acetate, fats, oils, waxes, fatty alcohols, hydroxypropylmethylcellulose phthalate, hydroxypropylmethylcellulose acetate succinate, cellulose acetate phthalate, starch acetate phthalate, polyvinylacetate phthalate, carboxymethylcellulose, methylcellulose phthalate, methylcellulose succinate, ethylcellulose, ethylcellulose succinate, gluten, ethylcarboxy-ethylecellulose, ethylacrylate-maleic acid anhydride copolymer, maleic acid anhydride-vinylmethylether copolymer, styrene-maleic acid anhydride copolymer, 2-ethyl-hexylacrylate maleic acid anhydride, crotonic acid-vinyl acetate copolymer, glutamic acid/glutamic acid ester copolymer, carboxymethylethylcellulose glycerol monooctanoate, cellulose acetate succinate, polyarginine, polyethylenes, polypropylenes, polyethylene oxide, polyethylene terephthalate, poly(vinylisobutylether), polyvinylchloride, polyurethane and mixtures thereof.

17. The process of claim 1 wherein the buffers are selected from the group consisting of phosphates, citrates, acetates, phthalates, bicarbonates, borates and mixtures thereof.

18. The process of claim 1 where the granulated material is dried by a process selected from the group consisting of fluidized-bed drying, rotary drying, tray drying, vacuum drying, radio-frequency drying and microwave drying.

* * * * *

UNITED STATES PATENT AND TRADEMARK OFFICE

CERTIFICATE OF CORRECTION

PATENT NO. : 7,607,596 B1
APPLICATION NO. : 12/072224
DATED : October 27, 2009
INVENTOR(S) : Isaac Gehebre-Sellassie et al.

It is certified that error appears in the above-identified patent and that said Letters Patent is hereby corrected as shown below:

Column 3, line 64, “(h)” should read -- (i) --.

Column 4, line 40, “feed” should read -- grinding/mixing --; line 45, delete “)”; line 49, “above or below” should read -- before or after --; line 54, “granulation/mixing” should read -- grinding/mixing --.

Column 6, line 9, “liquid” should read -- water --.

Column 9, lines 49-50, delete “or a second continuous granulator placed in series;” and insert the following text at the end of line 54:

-- or (I) a liquid/powder feed zone containing a first liquid/powder feed station ; (ii) a grinding/mixing zone containing a second liquid feed port located at an upstream portion of such zone; (iii) a mixer/granulator arranged in series with the twin-screw grinder/mixer; and (iv) a wet milling step; --.

Column 10, line 24, “(h)” should read -- (i) --.

Signed and Sealed this

Fifteenth Day of June, 2010

David J. Kappos

*Director of the United States Patent and Trademark Office*